United States Patent [19]
Hansen

[11] Patent Number: 5,824,919
[45] Date of Patent: Oct. 20, 1998

[54] SAMPLE CONDITIONING FLUE GAS PROBE

[75] Inventor: Neils Richard Stewart Hansen, East Croydon, England

[73] Assignee: Telegan Gas Monitoring Limited, England

[21] Appl. No.: 785,141

[22] Filed: Jan. 13, 1997

[30] Foreign Application Priority Data

Jan. 12, 1996 [GB] United Kingdom .................... 9600680

[51] Int. Cl.$^6$ .................................................. B01D 53/22
[52] U.S. Cl. ..................................... 73/863.23; 73/863.12
[58] Field of Search ........................... 73/863.11, 863.12, 73/863.23, 863.24, 863.81, 863.83; 55/267, 270, 315, 318, 320, 327, 332, 476

[56] References Cited

U.S. PATENT DOCUMENTS

| | | | |
|---|---|---|---|
| 3,367,850 | 2/1968 | Johnson | ................................ 73/863.23 |
| 4,705,543 | 11/1987 | Kertzman | .................................. 73/23.3 |
| 4,808,201 | 2/1989 | Kertzman | .................................. 73/863 |
| 5,237,881 | 8/1993 | Ross . | |
| 5,297,432 | 3/1994 | Traina et al. | ........................ 73/863.83 |

FOREIGN PATENT DOCUMENTS

| | | |
|---|---|---|
| 0419007 | 3/1991 | European Pat. Off. . |
| 2075673 | 11/1981 | United Kingdom . |

OTHER PUBLICATIONS

GASS —Gas Analysis Sampling System for CEMS Applications, product brochure from Perma Pure, Inc., date unknown.

Ambient Air Sample Conditioning System for Electro–Chemical Sensors, product brochure from Perma Pure, Inc., date unknown.

*Primary Examiner*—Robert Raevis
*Attorney, Agent, or Firm*—Dinsmore & Shohl LLP

[57] ABSTRACT

A flue gas probe that performs the sample conditioning functions of particulate and water removal at the point of sampling, i.e. within the flue or chimney. Particulate matter is removed by a porous ceramic filter positioned at one end of the probe. A polymeric drying element is also provided in order to remove water vapor from the sample by means of perevaporation.

18 Claims, 1 Drawing Sheet

SAMPLE CONDITIONING FLUE GAS PROBE

BACKGROUND OF THE INVENTION

A gas sample taken from a flue, or any structure that is employed to vent combustion products to atmosphere, usually contains high concentrations of water and particulates which frequently have to be removed before gaseous sample analysis can be performed. The chosen method of sample conditioning must ensure that these undesirable components are removed without altering the concentration of the gases to be analyzed.

Traditional methods of flue gas analysis separate the sample conditioning operations, which are normally performed at ambient temperature (10°–40° C.), from the point of sampling which is at an elevated temperature (frequently in the range 100°–800° C.). The dramatic change in temperature between the point of sampling and the sample conditioning unit causes water, which is present as steam in the flue gas, to condense in the inter-connecting sampling apparatus and gas analyzer. The components of the flue gas sample subsequently partition between the gaseous and condensed aqueous phases and the resultant gas mixture is usually non-representative of the original flue gas composition. Additionally the condensed water and dissolved components of the flue gas sample may damage the sampling apparatus and gas analyzer. Peltier-type thermoelectric heat pumps are frequently used to remove water from gas streams by condensing the water vapor at a cold surface and the subsequent gas analysis is subject to the errors associated with partitioning of analyte gaseous components.

Alternative sampling techniques employ heated sampling lines to ensure that the temperature of the flue gas sample remains above its dew point before being introduced to a sample conditioning unit, thereby preventing condensation of water in the interconnecting sampling apparatus. The principal disadvantages of employing heated sampling lines are the time, cost, complexity and increased power consumption, which frequently limit their incorporation into portable gas sampling and analyzing apparatus.

SUMMARY OF THE INVENTION

It is an object of the present invention to provide a flue gas sampling probe that can remove both particulates and water from the sample.

It is yet another object of the present invention to provide a flue gas sampling probe which can be inserted within or placed in close proximity to the flue being sampled.

The foregoing objects may be accomplished, in accordance with one aspect of the present invention, by providing a sample conditioning flue gas probe, comprising:
  (a) a porous filter for removing particulate matter from a flue gas sample;
  (b) a selectively water-permeable, polymeric drying tube having first and second surfaces; and
  (c) a support structure surrounding the drying tube; wherein the filter, drying tube and support structure are arranged such that a flue gas sample may be flowed through the filter and along a first surface of the drying tube, and such that a purge gas stream may be simultaneously flowed along a second surface of the drying tube, thereby allowing water from said flue gas to be transported across the surface of the drying tube into the purge gas without allowing the flue gas and purge gas to contact each other. The probe further preferably comprises a purge gas inlet and a purge gas outlet positioned such that a first end (i.e., the "hot end") of the probe may be positioned directly within flue being sampled, thereby allowing the heat of the flue gas to elevate the temperature of the drying tube to increase the rate of water transport across the drying tube wall by means of perevaporation. The filter is preferably positioned adjacent the first end of the probe so that any flue gas entering the probe must flow through the filter before contacting the drying tube. The drying tube preferably comprises a perfluorosulphonate ionomer. The particulate filter may comprise alumina or alumina-silicate particles bonded by glass, or in some instances a stainless steel filter.

The flue gas probe of the present invention also preferably has an outer protective sheath, and the drying tube and the support structure are arranged such that flue gas passing through the filter will be directed through the interior of the drying tube. The support structure may comprise concentric inner and outer tubes, and the drying tube may then be positioned within, and concentrically to the inner tube. In this manner, the purge gas inlet may be provided on the inner tube, and the purge gas outlet on the outer tube. If desired, however, this orientation may be reversed. The inner and outer tubes are also in fluid communication with each other (such as by one or more venting holes in the inner tube wall), thereby allowing the purge gas to be flowed through the inlet, into the interior of the inner tube along the outer surface of the drying tube, and thereafter into the outer tube and through the outlet. The venting hole(s) is positioned such that a purge gas can be flowed along the outer surface of the drying tube in a direction opposite to that of a flue gas flowing through the interior of the interior of the drying tube. More preferably, the venting hole(s) is positioned adjacent a first end of the inner and outer tubes, and the purge gas inlets and outlets are positioned adjacent a second end of the inner and outer tubes. A plurality of insulating spacers may also be positioned along the exterior surface of the drying tube, the spacers positioned so as to prevent the drying tube from contacting the inner tube.

A method of conditioning a flue gas sample for subsequent analysis is also provided, this method comprising:
  (a) providing a sample conditioning flue gas probe, comprising
    a porous filter for removing particulate matter the flue gas sample;
    a water-permeable, polymeric drying tube having first and second surfaces; and
    a support structure surrounding the drying tube;
  (b) positioning the probe within the flue;
  (c) flowing a sample of the flue gas through the filter and along a first surface of the drying tube, such that the flue gas will heat the drying tube; and
  (d) flowing a purge gas along a second surface of the drying tube, such that the purge gas does not contact the flue gas; such that the filter removes particulates in the flue gas, and water is transported across the surface of the drying tube into the purge gas without allowing the flue gas and purge gas to contact each other. The flue gas sample is preferably flowed through the interior of the drying tube, and the purge gas is flowed along the exterior surface of the drying tube in an opposite direction.

DETAILED DESCRIPTION OF THE PREFERRED EMBODIMENTS

Figure 1:
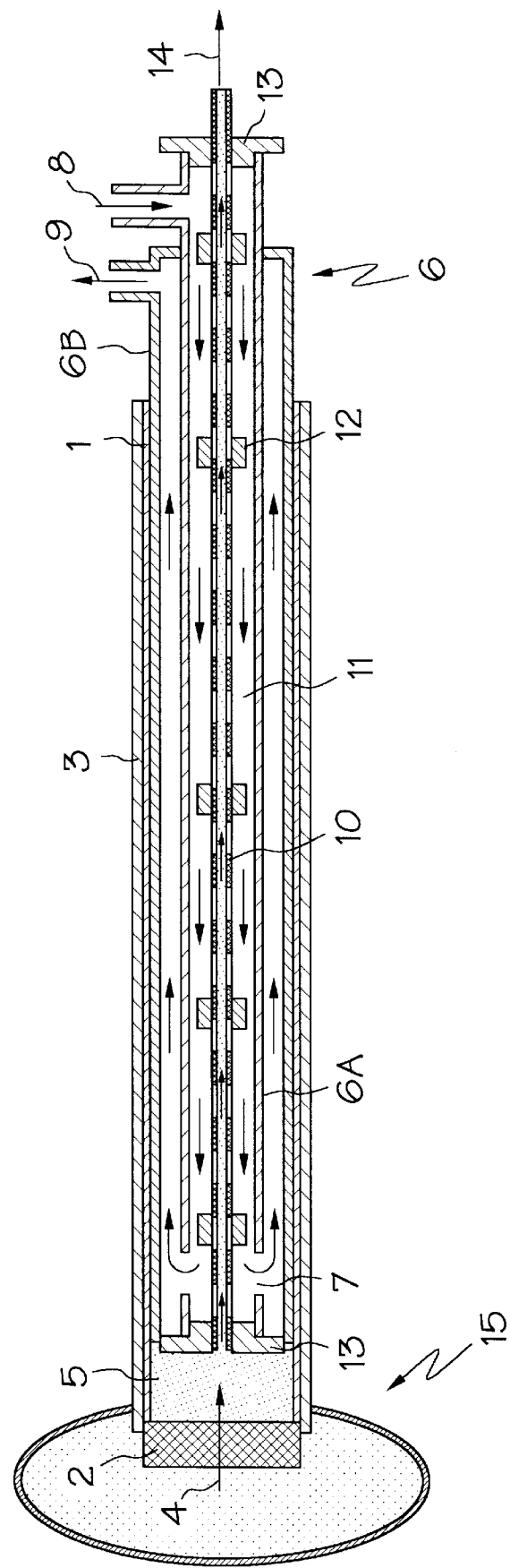
FIG. 1 is cross-sectional view of a flue gas probe according to the present invention.

The present invention provides a flue gas sampling probe which overcomes the deficiencies of the prior art sampling and conditioning probes. The principle advantage of the sample conditioning flue gas probe of the present invention is that the probe can perform the combined sample conditioning operations of particulate and water removal directly at a flue or other source of gas to be analyzed, thereby ensuring that the concentration of analyte gases within the flue gas sample remains constant and representative of the original flue gas without the requirement for heated sampling lines. In fact, one end of the probe of the present invention is inserted directly into the probe, and the sample conditioning is performed within the probe itself, thereby greater simplifying the sampling process.

According to the present invention there is provided a flue gas probe comprising a protective outer sheath incorporating a porous particulate filter at one end through which any flue gas must be transported before being transported further along the probe, and a gas tight inner support structure. The end having the particulate filter may be inserted directly into the flue. The inner support structure incorporates a selectively water-permeable polymeric barrier, preferably in the form of one or more tubes, which may employ the indirect heat from the flue gas when the probe one end of the probe is inserted directly into the flue being sampled. An inner support structure is configured to allow the passage of the flue gas sample stream along one surface of the polymeric barrier, and a purge gas stream across the opposite surface, without permitting the two gas streams to contact each other. Water is transported across the polymer where it evaporates into the relatively dry purge gas stream which then transports the water away from the polymer and out of the probe.

The porous filter, which is preferably ceramic in nature, removes particulates from the flue gas sample at the point of sampling, thereby preventing the deposition of particulate matter along the sampling lines and protecting the delicate polymer drying tube from particulate damage. Such deposition of particulate matter provides an extremely high surface area for the absorption of gaseous components from the flue gas, which could result in a non-representative flue gas sample. Thus, it is preferred that the filter be positioned at or adjacent to the end of the probe which is to be inserted into the flue. In this manner, particulates are removed from the flue gas sample prior to the sample contacting the delicate drying tube(s). In addition, if the filter is positioned at one end of the probe, the user will be able to readily observe any buildup of particulate matter which may necessitate a cleaning or replacement of the filter.

The principal advantage of incorporating a polymeric drying element in the structure of the flue gas probe is that the thermal energy of the flue gas can be used to increase the temperature of the polymeric material, thereby increasing the rate of water transport across this barrier and hence the efficiency of water removal from the sample gas. No additional power source is required to heat the polymeric material, thereby providing a probe which may be employed in portable applications. The probe only requires connection to a relatively dry purge gas stream, which will frequently be ambient air optionally dried using a suitable desiccant, or dry gas from a compressed gas cylinder. This gas stream has the additional benefit of cooling the polymer to temperatures below the maximum permissible operating temperature (160° C. for the preferred polymer), thereby enabling the flue gas probe to be inserted directly into a flue and perform sample conditioning operations on flue gas streams at much higher temperatures. The configuration of the probe of the present invention also permits one end of the probe to be connected to a purge gas source, while still permitting the other end to be inserted into the flue being sampled.

Flue gas samples for which the probe of the present invention may be employed will typically be at a pressure slightly lower than atmospheric pressure due to the Venturi effect of the flue gas being transported along the flue, but the probe of the present invention may be employed for pressures between 0.1 and 2 bar. The temperature of the flue gas sample can be in the range 10°–800° C., and can contain, among other things, the following gases in any concentration and in any possible combination:

a) atmospheric gases, including water vapor,
b) unburned fuels, including hydrocarbons, aldehydes, esters,
c) oxides formed from the complete or partial combustion of carbon, nitrogen and sulfur containing fuels, including carbon monoxide, carbon dioxide, sulfur dioxide, sulfur trioxide, nitrogen monoxide, nitrogen dioxide.
d) halogenated carbon compounds, hydrogen halides, free chlorine or acid chlorides
e) sulfur-containing compounds such as hydrogen sulfide, mercaptanes, hydrogen cyanide,
f) alcohols, aldehydes, ketones, organic acids and ethers, The protective outer sheath should be fabricated from either a single material, or a combination of materials that provide the properties of:

1) chemical resistance to the components of the flue gas;
2) mechanical strength for a portable probe that can withstand frequent handling;
3) thermal properties such as the ability to withstand the large thermal gradient across its structure, high maximum operational temperatures (up to 800° C.), and the thermal shock of raising the temperature from ambient (10°–40° C.) to the high temperatures of the flue gas (up to 800° C.); and
4) the ability to maintain a gas tight seal between: (a) the filter and the protective outer sheath, (b) the gas seals, the inner structure of the probe and the polymer drying tube, and (c) the outer sheath and the inner structure of the probe following thermal expansion.

The above requirements may be met by the combined use of a ceramic material to provide refractory properties such as thermal insulation and high temperature operation, and stainless steel to provide mechanical strength and to enable facile fabrication. Suitable ceramic materials include aluminum and silicon oxides referred to hereafter as alumina and silica, respectively.

The porous particulate filter is preferably fabricated from alumina or alumina-silicate particles bonded by glass, and should have a minimum retention efficiency of 98% at 10 microns (Grade P6 according to BS 2831 Test Dust No.2, wherein BS 2831 refers to the British Standard for testing the retention efficiency of filter materials). Such a material is suitably inert and can withstand the elevated temperatures of a flue gas environment (specifically, hot gases up to 900°C.). These filters are available from, for example, Fairey Industrial Ceramics Ltd., of Staffordshire, England.

The dry purge gas stream employed with the probe of the present invention may be any gas that is below its dew point, and is also inert to the polymeric tubing, the thermally insulating spacers, or the inner support structure which the purge gas might contact. The purge gas stream is preferably at a pressure of between 0.05 and 4 bar, and the drier the gas (i.e., the lower its dew point or relative humidity), the greater the drying efficiency of the probe will be (due to the purge gas' increased capacity to take up water from the surface of the drying tube). Thus, the purge gas is preferably well below its dew point. The flow rate of the dry carrier purge gas stream is dependent upon the pressure limits and the dimensions of the probe. The dry purge gas stream performs the dual role of transporting water vapor away from the polymeric drying element while simultaneously cooling the drying element, and the ability of the purge gas stream to perform both these functions is proportional to the actual volumetric purge gas flow. The ratio of the flow rates of the purge and sample gas streams should be high enough to remove sufficient heat from the system to protect the polymer drying element and to transport sufficient water vapor away from the surface of the polymer to significantly reduce the water content of the sample gas stream by the process of perevaporation, and it is preferable that the purge gas flow rate be at least twice that of the flue sample. The removal of water from the sample gas will also be more efficient if the purge gas is at a reduced pressure with respect to the sample gas stream.

The polymeric drying element preferably comprises a selectively water-permeable material which allows the selective permeation of water through the polymeric structure by the process of perevaporation, i.e. the process by which water is transported across a selectively water permeable barrier under the influence of a humidity gradient. In these materials, water molecules are transported from the wetter surface of the polymer to the dryer surface, while other components of the gases are not transported. In this manner, if a relatively humid gas is flowed across one surface of the polymer, and a dry gas along the other surface, water molecules will be transported across the polymer from the humid gas to the dry gas. The rate of water transfer is also temperature dependant, and thus it is desirable that the polymer be elevated to the highest possible temperature. One particular class of polymers which may be employed for this purpose are perfluorosulphonate ionomers, and a particularly preferred perfluorosulphonate ionomer is Nafion®, a trademark of DuPont de Nemours and Company.

The gas seals of the probe are preferably made from polytetrafluoroethylene, referred to hereafter as P.T.F.E., which may be used at high operating temperatures (up to 450° C.) and is also chemically inert to the expected components of the flue gas sample. Alternatively, other inert polymeric materials may be employed such as Tefzel®, Halar®, or Kynar®. The gas seals should be insulated from the flue gas by the protective outer sheath and be in contact with the cool dry purge gas stream to ensure that the P.T.F.E. seal is held below its maximum operating temperature of 450° C. It should be noted that the temperature of the gas seals at the end of the probe positioned away from the flue will be greatly reduced, and thus the high temperature-resistance property of these seals is not as critical. The thermally-insulating spacers fitted to the polymeric drying element (further described below) should also be made of a thermally insulating material that can withstand temperatures up to 200° C., and thus stainless steel or P.T.F.E. may be employed for this purpose.

If desired, thermocouples (or other temperature measuring devices) may be employed to monitor the temperature of the flue gas or the temperature of the polymeric drying tube(s) for information purposes, e.g. efficiency calculations, and/or as a protective measure to ensure that the temperature of the polymer drying element does not exceed the maximum permissible operating temperature (160° C. for the preferred polymer).

A specific embodiment of the invention will now be described by way of example with reference to the accompanying drawing in which:

FIG. 1 shows in cross-section a flue gas probe according to the present invention, wherein the flow direction of the flue gas sample stream is indicated by solid black arrows, and the purge gas flow is indicated by the arrows having a black outline. Excluding inlet 8 and outlet 9 (connections for the purge gas stream) and the venting holes in the inner structure 7, the preferred embodiment of the flue gas probe has axial circular symmetry along its entire length. It should be noted, however, that other embodiments not having such axial symmetry are contemplated (e.g., multiple drying tubes).

Referring to FIG. 1 in detail, the gas probe comprises an outer protective sheath 1 (304-L stainless steel length 500 mm, O.D. 9.5 mm, I.D. 8.5 mm) that incorporates a porous ceramic filter 2 (Pyrolith™ Grade P6, alumino-silicate particles bonded by glass, length 4 mm, diameter 9 mm, and available from Fairey Industrial Ceramics) sealed to, or within one open end of the outer protective sheath 1, such as by using an inorganically-bonded, stainless steel adhesive (Durabond™ 954 stainless steel adhesive). It should be noted that all of the dimensions provided herein are merely exemplary, and are not intended to limit the scope of the present invention in any way. Filter 2 should be sealed tightly to the outer sheath to ensure that no gases can escape. The end 15 of the probe having filter 2 is referred to as the "hot end", since it will be inserted directly into the flue being sampled. The external surface of outer protective sheath 1 is preferably covered with a thermally-insulating ceramic fiber coating 3. Coating 3 can, for example, comprise a high strength woven ceramic sleeving such as 395-Thermeez, or a ceramic fiber coating such as Rescor™ 901 composite of high purity alumina based ceramic fibers and inorganic binder. Alternatively, or additionally, a ceramic fiber coating may also be positioned between the outer sheath and the internal support structure described below.

As will be further understood, the flue gas sample stream in region 5 that contacts the inner surface of outer protective sheath 1 must pass through the ceramic filter 2 before being transported further along the flue gas probe. The flue gas sample stream in region 5 will have thus have an identical gaseous composition to the flue gas 4, but will have a greatly reduced concentration of particulate matter following filtration by ceramic filter 2. In addition, the size of region 5 may be varied in order to ensure that the flue gas has been sufficiently cooled prior to its contacting the polymeric drying element. Thus, the distance between filter 2 and inner support structure 6 (further described below), in other words the length of region 5, may be modified according to the type of service contemplated. If the flue has a temperature approaching the maximum of 800° C., the length of region 5 should be sufficient to ensure that the hot end of the probe may be inserted into the flue the desired distance, while also ensuring that the distance between the flue wall and support structure 6 will be sufficient (preferably at least about 12 cm). In other words, a probe intended for high temperature use will be configured such that when the hot end of the probe is inserted into the flue, flue, gas entering the probe will not contact the support structure (and hence the polymeric drying tubes) until it has traveled the specified minimum distance along the probe beyond the flue wall. This will allow the flue gas to cool to a suitable temperature (between 120° C. and 300° C., preferably less than about 150° C.) thereby ensuring that the polymeric drying element is not damaged and that there is sufficient heat to warm the drying element to the desired temperature. Since the temperature of the flue gas will drop about 400° C. for every 10 cm it travels within region 5 beyond the flue wall, this can be readily accomplished by minor changes in the dimensions of the probe.

The temperature of the flue gas contacting the polymeric drying tube(s) is also a function of how far the probe is inserted into the flue. Thus, the further that the hot end is inserted into the probe (all other dimensions being equal), the hotter the flue gas will be which contacts the polymeric drying tube. It is preferred, however, that the hot end be inserted into the probe a distance equal to between $1/3$ and $2/3$ of the diameter of the flue in order to ensure a representative sample.

Inner support structure 6 may be fabricated from two concentric tubes of different lengths which are preferably sealed at either end (such as by using flat rings of suitable dimensions). Thus, inner support structure 6 comprises inner tube 6A and outer tube 6B. Inner tube 6A preferably has one or more venting holes at one end which provide fluid communication between the interior of inner tube 6A and the interior of outer tube 6B. In this fashion, gas may be flowed along the interior of inner tube 6A in a first direction towards said venting holes, and thereafter escaping through the venting holes into outer tube 6B. The gas may then flow in the opposite direction along the interior of outer tube 6B (and therefore along the outer surface of inner tube 6A). As detailed below, this arrangement allows the purge gas inlets and outlets to be positioned at the same end of the probe.

In the specific embodiment shown, inner tube 6A (stainless steel 304-L, I.D. 4 mm, O.D. 5 mm, length 295 mm) has four venting holes 7 of 1.5 mm diameter drilled alternately 10 mm and 15 mm from the end nearest the ceramic filter 2 as shown in FIG. 1, and another hole 3 mm in diameter drilled 10 mm from the opposite end for gas inlet 8. Inlet 8 allows gas (such as the purge gas), to enter the interior of inner tube 6A and flow towards venting holes 7. Outer tube 6B (304-L stainless steel, I.D. 7 mm, O.D. 8 mm, length 280 mm) has a hole 3 mm in diameter drilled 10 mm from the end furthest from the ceramic filter 2 for gas outlet 9. Gas outlet 9 allows the purge gas to escape from the inner support structure. Gas inlet 8 and outlet 9 are positioned at the end of the probe opposite particulate filter 2, as shown in FIG. 1. This arrangement of the inner and outer tubes of the support structure, and the inlet and outlet of each in this manner allows the purge gas inlets to remain accessible even when the end having filter 2 is positioned within or in close proximity to the flue or other gas source being sampled. The two ends of the inner and outer tubes nearest the ceramic filter 2 are sealed against a flat ring (stainless steel 304-L, thickness 0.5 mm, O.D. 8 mm, I.D. 4 mm). At the opposite end of outer tube 6B and 15 mm from the opposite end of inner tube 6A, the inner and outer tubes are likewise sealed against a flat ring (stainless steel 304-L, thickness 0.5 mm, O.D. 8 mm, I.D. 5 mm).

The above arrangement wherein the purge gas flows into inner tube 6A towards hot end 15, and then away from hot end 15 through outer tube 6B, is only the preferred configuration. Thus, it is possible to reverse this flow if desired, such that the purge gas flows into the probe through outer tube 6B towards hot end 15, and then away from hot end 15 through inner tube 6B. Applicant has found, however, that the configuration of FIG. 1 is preferred since it allows for increased heat removal by the purge gas.

The polymeric drying element preferably comprises one or more polymeric drying tubes 10. In the embodiment shown, drying tube 10 is a tubular element comprising a selectively water-permeable polymeric material such as a perfluorosulphonate ionomer (e.g., Nafion™). Drying tube 10 and the spacers described below should be at least as long as inner tube 6A and outer tube 6B in order to ensure that the flue gas flowing therethrough will not contact the purge gas (in the example shown, drying tube 10 has a length of 300 mm, O.D. 1.27 mm, I.D. 1.00 mm). Polymeric drying tube 10 separates the flue gas sample stream from the purge gas stream 11 which enters the probe through the purge gas inlet 8 and exits through the purge gas outlet 9.

Drying tube 10 is preferably terminated at both ends by two supports (not shown) which are preferably stainless steel or P.T.F.E. (length 25 mm, O.D. 1.6 mm, I.D. 1.27 mm). These inserts may be merely small tubes which are rammed into the ends of the softer polymeric drying tube to provide mechanical support and a fixation point for the probe assembly. A plurality of thermally-insulating spacers 12, preferably made from P.T.F.E., may be provided along the length of the polymeric drying tube 10 to prevent drying tube 10 from contacting inner support structure 6. These spacers act to protect the delicate polymer drying tube, and to ensure efficient transfer of water vapor across the surface of the drying tube. In the specific example shown, five such spacers 12 are provided, each being 2 mm in length, 3 mm in diameter, with a 1.5 mm radial slot cut 2 mm into the body of each spacer.

It is contemplated that multiple drying tubes may be employed in the present invention, and thus three such tubes may be provided within inner tube 6A. The tubes may be arranged in any fashion, however it is preferred that they be arranged symmetrically within inner tube 6A. Multiple drying tubes will allow for higher flow rates and/or greater residence time, and therefore provide improved water removal. As yet another alternative, it also contemplated that the purge gas may be flowed on the inside of the polymeric drying tube, with the flue gas on the outside.

Two inert, thermally-insulating receivers 13 (preferably made from P.T.F.E.) are employed to form a gas tight seal between the inner support structure 6 and the polymeric drying tube 10, thereby preventing the gas sample stream from coming in contact with the purge gas stream. The receivers 13 each have circular symmetry, and a hole running axially along the entire length to receive the polymeric drying tube 10. In the example shown, each receiver 13 has a total length of 4 mm and the hole therethrough is 1.5 mm in diameter. From the edge of the receiver to a point 2 mm along its length the diameter is 4 mm and for the remaining 2 mm of the length of the receiver the diameter is 7 mm. The ends of the drying tube 10 should be inserted into the receivers 13 so that the narrow section of each receiver is nearest the center of the polymeric drying tube 10 as shown. The narrow section of each receiver 13 is inserted into the inner support structure 6 to locate the polymeric drying tube 10 within the interior of inner tube 6A, and to form a gas tight seal between the receiver 13, the polymeric drying tube 10 and the inner support structure 6.

The outer protective sheath and ceramic filter may also be separated or isolated from the inner support structure and polymer drying tube. In this manner, the filter may be cleaned merely by applying a high gas pressure gradient across the filter.

Use of the sample conditioning flue gas probe of the present invention is straightforward. The end of the probe is inserted directly into the flue or chimney to be sampled, preferably to the distance described previously while ensuring that the flue gas temperature will not exceed the specified maximum for the drying tube at the point where the flue gas first contacts the drying tube. A purge gas source is then connected to inlet 8 so that the purge gas will flow through the interior of inner tube 6A towards filter 2, through venting holes 7 into outer tube 6B, and along the interior of outer tube 6B towards outlet 9. Suitable purge gases include dried ambient air (e.g., ambient air at 20° C. which has been dried to a dew point of −15° C. using a desiccant such as silica gel). Compressed dry gas may also be used.

Once the probe is so positioned, flue gas will flow through particulate filter 2, and through the interior of polymer drying tube 10 away from filter 2. The flue gas will thus flow along the one surface of the polymer drying tube, while the purge gas is flowing countercurrent along the opposite surface. Water ions present in the flue gas will then be transported across the surface of the polymer drying tube, and into the purge gas by means of perevaporation. The heated flue gas will also elevate the temperature of the polymer drying tube, thereby improving the rate of water transport. The purge gas, on the other hand, will ensure that the polymer drying tube temperature does not become too high. Flue gas leaving the probe (14) will thus have considerably less particulate matter and significantly less water vapor, and may be flowed towards analytical equipment for an analysis of the flue gas components. Applicant's testing has demonstrated that effective conditioning of a 5–6 $cm^3 s^{-1}$ flue gas sample having a dew point greater than 60° C. can be obtained using a probe of the present invention having the herein-recited dimensions using a purge gas stream of ambient air at 20 C. which has been dried to a dew point of −15° C. using a desiccant such as silica gel, flowing at a rate of 15 $cm^3 s^{-1}$.

The foregoing description of preferred embodiments is by no means exhaustive of the variations in the present invention that are possible, and has been presented only for purposes of illustration and description. Obvious modifications and variations will be apparent to those skilled in the art in light of the teachings of the foregoing description without departing from the scope of this invention. Thus, it is intended that the scope of the present invention be defined by the claims appended hereto.

What I claim is:

1. A sample conditioning flue gas probe, comprising:
   (a) a selectively water-permeable, polymeric drying tube having first and second surfaces; and
   (b) a support structure surrounding said drying tube, said support structure comprising concentric inner and outer tubes in fluid communication with each other, wherein said drying tube is positioned within said inner tube; and
   (c) a purge gas inlet and a purge gas outlet, each positioned on one of said inner and outer tubes such that said inlet and outlet are not positioned on the same tube;
   wherein said drying tube and support structure are arranged such that a flue gas sample may be flowed through said drying tube, and such that a purge gas stream may be simultaneously flowed through said inlet, through said inner tube along the outer surface of said drying tube, and thereafter through said outlet, thereby allowing water from said flue gas to be transported across the surface of the drying tube into said purge gas without allowing the flue gas and purge gas to contact each other.

2. The flue gas probe of claim 1, wherein said purge gas inlet and said purge gas outlet are positioned such that a first end of said probe may be inserted into a flue being sampled, thereby allowing the heat of the flue gas to elevate the temperature of said drying tube and increase the rate of water transport.

3. The flue gas probe of claim 2, further comprising a porous filter for removing particulate matter from a flue gas sample, wherein said filter is positioned adjacent said first end of said probe so that any flue gas entering said probe must flow through said filter before contacting said drying tube.

4. The flue gas probe of claim 3, further comprising an outer protective sheath.

5. The flue gas probe of claim 4, wherein said drying tube comprises a perfluorosulphonate ionomer.

6. The flue gas probe of claim 1, wherein said purge gas inlet is on said inner tube and said purge gas outlet is on said outer tube, such that said purge gas may be flowed through said inlet, into the interior of the inner tube along the outer surface of said drying tube, and thereafter into said outer tube and through said outlet.

7. The flue gas probe of claim 6, wherein said inner tube has at least one venting hole providing said fluid communication between said inner and outer tubes, and wherein said purge gas inlets and outlets, and said at least one venting hole are positioned such that a purge gas can be flowed along the outer surface of said drying tube in a direction opposite to that of a flue gas flowing through the interior of said drying tube.

8. The flue gas probe of claim 7, wherein said at least one venting hole is positioned adjacent a first end of said inner and outer tubes, and wherein said purge gas inlets and outlets are positioned adjacent a second end of said inner and outer tubes.

9. The flue gas probe of claim 6, wherein said filter comprises alumina or alumina-silicate particles bonded by glass.

10. The flue gas probe of claim 6, further comprising a plurality of thermally insulating spacers positioned along the exterior surface of said drying tube, said spacers positioned so as to prevent said drying tube from contacting said inner tube.

11. The flue gas probe of claim 1, wherein said purge gas inlet is on said outer tube and said purge gas outlet is on said inner tube, such that said purge gas may be flowed through said inlet, through said outer tube into the interior of said inner tube, along the outer surface of said drying tube, and thereafter through said outlet.

12. A sample conditioning flue gas probe having first and second ends, comprising:
    (a) a selectively water-permeable, polymeric drying tube having first and second surfaces;
    (b) a support structure surrounding said drying tube; and
    (c) a purge gas inlet and a purge gas outlet on said support structure;
    wherein said drying tube and support structure are arranged such that a flue gas sample may be flowed through the interior of said drying tube, and such that a purge gas stream may be simultaneously flowed into said purge gas inlet, through said support structure along the outer surface of said drying tube, and thereafter exiting through said outlet, thereby allowing water from said flue gas to be transported across the surface of the drying tube into said purge gas without allowing the flue gas and purge gas to contact each other, and wherein said inlet and outlet are both positioned adjacent said second end of said probe, such that said first end of said probe may be inserted into a flue being sampled.

13. The flue gas probe of claim 12, further comprising an outer protective sheath and a porous filter for removing particulate matter from a flue gas sample, said support structure positioned within said outer protective sheath and said filter positioned adjacent the first end of said probe, wherein said first end of said probe may be inserted into a flue being sampled, whereby the flue gas being sampled will be directed through said filter prior to contacting said drying tube, and also thereby allowing the heat of the flue gas to elevate the temperature of said drying tube in order to increase the rate of water transport.

14. The flue gas probe of claim 12, wherein said purge gas inlet and said purge gas outlet are configured such that a purge gas may be flowed through said support structure in a direction opposite that of said flue gas.

15. A method of conditioning a flue gas sample for subsequent analysis, comprising:

(a) providing a sample conditioning flue gas probe having first and second ends, said probe comprising a porous filter for removing particulate matter said flue gas sample;

a selectively water-permeable, polymeric drying tube having first and second surfaces;

a support structure surrounding said drying tube; and a purge gas inlet and a purge gas outlet on said support structure, wherein said inlet and outlet are both positioned adjacent said second end of said probe, such that said first end of said probe may be inserted into a flue being sampled;

(b) positioning said first end of said probe within said flue;

(c) flowing a sample of said flue gas through said filter and along a first surface of said drying tube, such that said flue gas will heat said drying tube; and (d) flowing a purge gas through said inlet into said probe, along a second surface of said drying tube, such that said purge gas does not contact said flue gas, and thereafter through said outlet;

such that said filter removes particulates in said flue gas, and water is transported across the surface of the drying tube into said purge gas without allowing the flue gas and purge gas to contact each other.

16. The method of claim 15, wherein said flue gas sample is flowed through the interior of said drying tube, and said purge gas is flowed along the exterior surface of said drying tube.

17. The method of claim 16, wherein said flue gas sample and said purge gas are flowed along the interior and the exterior of said drying tube, respectfully, in opposite directions.

18. The method of claim 16, wherein said drying tube comprises a perfluorosulphonate ionomer.

* * * * *